United States Patent
DeVore et al.

(10) Patent No.: US 12,304,974 B2
(45) Date of Patent: May 20, 2025

(54) HYALURONIC ACID-COLLAGEN COPOLYMER COMPOSITIONS AND MEDICAL APPLICATIONS THEREOF

(71) Applicant: Shanghai Qisheng Biological Preparation Co., Ltd., Shanghai (CN)

(72) Inventors: Dale P. DeVore, Chelmsford, MA (US); Jiaxun Zhu, Shanghai (CN)

(73) Assignee: Shanghai Qisheng Biological Preparation Co., Ltd., Shanghai (CN)

( * ) Notice: Subject to any disclaimer, the term of this patent is extended or adjusted under 35 U.S.C. 154(b) by 0 days.

(21) Appl. No.: 18/089,788

(22) Filed: Dec. 28, 2022

(65) Prior Publication Data

US 2023/0203207 A1    Jun. 29, 2023

Related U.S. Application Data

(60) Provisional application No. 63/294,164, filed on Dec. 28, 2021.

(51) Int. Cl.
| | |
|---|---|
| *A61K 31/728* | (2006.01) |
| *A61K 31/726* | (2006.01) |
| *A61K 31/727* | (2006.01) |
| *C08B 37/00* | (2006.01) |
| *C08B 37/08* | (2006.01) |
| *C08B 37/10* | (2006.01) |
| *C08G 81/00* | (2006.01) |
| *C12P 13/08* | (2006.01) |

(52) U.S. Cl.
CPC .......... *C08B 37/0063* (2013.01); *C12P 13/08* (2013.01)

(58) Field of Classification Search
CPC ... C08B 37/0063; C08B 37/0072; C12P 13/08
See application file for complete search history.

(56) References Cited

U.S. PATENT DOCUMENTS

| | | |
|---|---|---|
| 4,141,973 A | 2/1979 | Balazs |
| 4,164,559 A | 8/1979 | Dunn |
| 4,291,013 A | 9/1981 | Wahlig |
| 4,347,234 A | 8/1982 | Wahlig |
| 4,424,208 A | 1/1984 | Wallace |
| 4,488,911 A | 12/1984 | Luck |
| 4,582,640 A | 4/1986 | Smestad |
| 4,582,865 A | 4/1986 | Balazs |
| 4,592,864 A | 6/1986 | Miyata |
| 4,605,691 A | 8/1986 | Balazs |
| 4,642,117 A | 2/1987 | Nguyen |
| 4,713,446 A | 12/1987 | DeVore |
| 4,716,154 A | 12/1987 | Maelson |
| 4,716,224 A | 12/1987 | Sakurai |
| 4,784,990 A | 11/1988 | Nimrod |
| 4,803,075 A | 2/1989 | Wallace |
| 4,851,513 A | 7/1989 | DeVore |
| 4,883,864 A | 11/1989 | Scholz |
| 4,937,270 A | 6/1990 | Hamilton |
| 4,963,666 A | 10/1990 | Maelson |
| 4,969,912 A | 11/1990 | Kelman |
| 4,992,226 A | 2/1991 | Piez |
| 5,017,229 A | 5/1991 | Burns |
| 5,067,961 A | 11/1991 | Kelman |
| 5,099,013 A | 3/1992 | Balazs |
| 5,103,840 A | 4/1992 | Kavoussi |
| 5,104,957 A | 4/1992 | Kelman |
| 5,162,430 A | 11/1992 | Rhee |
| 5,166,331 A | 11/1992 | Della Valle |
| 5,201,764 A | 4/1993 | Kelman |
| 5,219,895 A | 6/1993 | Kelman |
| 5,292,802 A | 3/1994 | Rhee |
| 5,304,147 A | 4/1994 | Johnson |
| 5,306,500 A | 4/1994 | Rhee |
| 5,316,926 A | 5/1994 | Brown |
| 5,322,802 A | 6/1994 | Baliga |
| 5,324,519 A | 6/1994 | Dunn |
| 5,324,775 A | 6/1994 | Rhee |
| 5,328,955 A | 7/1994 | Rhee |
| 5,332,809 A | 7/1994 | Della Valle |
| 5,354,336 A | 10/1994 | Kelman |
| 5,356,883 A | 10/1994 | Kuo |
| 5,366,498 A | 11/1994 | Brannan |
| 5,376,375 A | 12/1994 | Rhee |

(Continued)

FOREIGN PATENT DOCUMENTS

| | | |
|---|---|---|
| CN | 105879124 | 8/2016 |
| CN | 109224127 | 1/2019 |

(Continued)

OTHER PUBLICATIONS

Lu, CN107441561 (2017)—cited in IDS filed Jul. 24, 2023, USPTO English machine translation 2024, 13 pages (Year: 2017).*
Tang et al, "A free-standing multilayer film as a novel delivery carrier of platelet lysates for potential wound-dressing applications," Biomaterials 255: 120138, pp. 1-15 (2020) (Year: 2020).*
Lin, Yung-Kai et al., "Studies of novel hyaluronic acid-collagen sponge materials composed of two different species of type I collagen." Journal of Biomaterials Applications, Jan. 2007, vol. 21, No. 3, pp. 265-281.
Meyer, Karl, et al., "The polysaccharide of the vitreous humor." Journal of Biological Chemistry, 1934, 107, pp. 629-634.
Nobuhiko, Yui, et al., "Inflammation responsive degradation of crosslinked hyaluronic acid gels." Journal of Controlled Release, vol. 22, No. 2, 1992, pp. 105-116.

(Continued)

*Primary Examiner* — Julie Ha
*Assistant Examiner* — Kristina M Hellman
(74) *Attorney, Agent, or Firm* — Fitch, Even, Tabin & Flannery LLP

(57) ABSTRACT

The present disclosure relates to glycosaminoglycan-collagen copolymer compositions (such as hyaluronic acid-collagen copolymers and heparosan-collagen copolymer compositions) and medical applications thereof for augmenting soft tissue defects. The copolymer composition may be injected into tissues to correct defects or deficiencies, such as skin wrinkles, scars, and folds in dermal tissues.

21 Claims, 1 Drawing Sheet

(56) References Cited

U.S. PATENT DOCUMENTS

Figure 1:
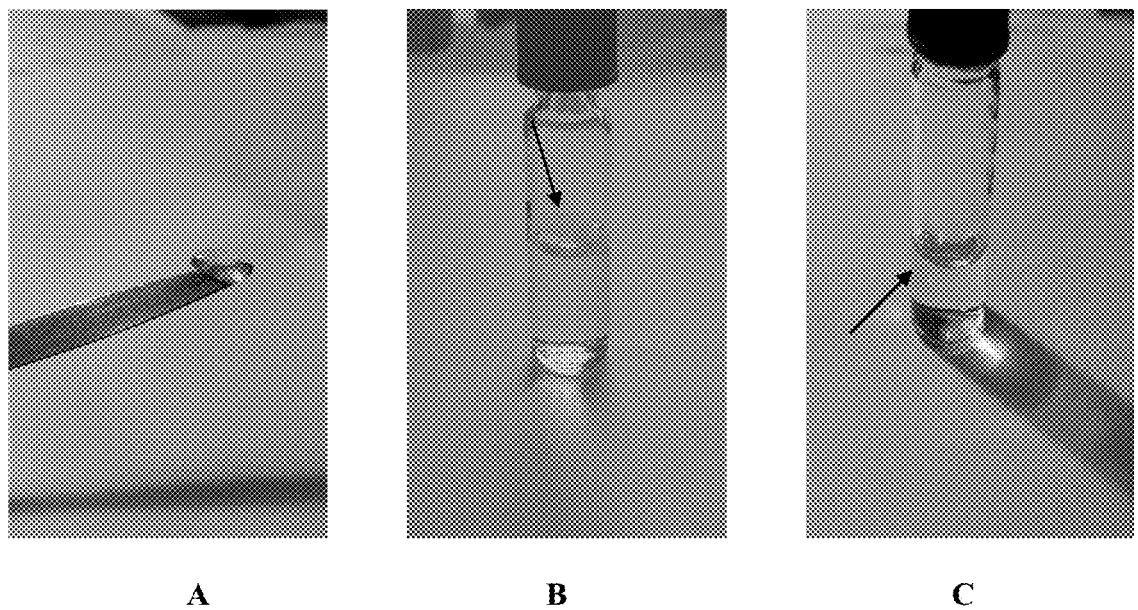

| | | | |
|---|---|---|---|
| 5,383,930 A | 1/1995 | Brannan |
| 5,411,874 A | 5/1995 | Ellwood |
| 5,413,791 A | 5/1995 | Rhee |
| 5,428,024 A | 6/1995 | Chu |
| 5,436,135 A | 7/1995 | Tayot |
| 5,446,091 A | 8/1995 | Rhee |
| 5,475,052 A | 12/1995 | Rhee |
| 5,476,515 A | 12/1995 | Kelman |
| 5,480,427 A | 1/1996 | Kelman |
| 5,492,135 A | 2/1996 | DeVore |
| 5,502,081 A | 3/1996 | Kuo |
| 5,510,418 A | 4/1996 | Rhee |
| 5,527,893 A | 6/1996 | Burns |
| 5,550,188 A | 8/1996 | Rhee |
| 5,559,104 A | 9/1996 | Romeo |
| 5,565,519 A | 10/1996 | Rhee |
| 5,591,444 A | 1/1997 | Boss, Jr. |
| 5,631,243 A | 5/1997 | Kelman |
| 5,660,850 A | 8/1997 | Boss, Jr. |
| 5,665,372 A | 9/1997 | Boss, Jr. |
| 5,760,200 A | 6/1998 | Miller |
| 5,783,691 A | 7/1998 | Maelson |
| 5,800,541 A | 9/1998 | Rhee |
| 5,807,581 A | 9/1998 | Rosenblatt |
| 5,823,671 A | 10/1998 | Mitchell |
| 5,824,333 A | 10/1998 | Scopelianos |
| 5,830,708 A | 11/1998 | Naughton |
| 5,840,848 A | 11/1998 | Sturrock |
| 5,858,390 A | 1/1999 | Boss, Jr. |
| 5,861,486 A | 1/1999 | DeVore |
| 5,874,500 A | 2/1999 | Rhee |
| 5,925,626 A | 7/1999 | Della Valle |
| 6,013,679 A | 1/2000 | Kuo |
| 6,051,648 A | 4/2000 | Rhee |
| 6,071,530 A | 6/2000 | Polson |
| 6,129,761 A | 10/2000 | Hubbell |
| 6,150,461 A | 11/2000 | Takei |
| 6,161,544 A | 12/2000 | DeVore |
| 6,166,130 A | 12/2000 | Rhee |
| 6,284,284 B1 | 9/2001 | Naughton |
| 6,323,278 B2 | 11/2001 | Rhee |
| 6,337,389 B1 | 1/2002 | Wolfinbarger, Jr. |
| 6,458,889 B1 | 10/2002 | Trollsas |
| 6,511,958 B1 | 1/2003 | Atkinson |
| 6,521,244 B1 | 2/2003 | Kanesaka |
| 6,534,591 B2 | 3/2003 | Rhee |
| 6,682,760 B2 | 1/2004 | Noff |
| 6,833,408 B2 | 12/2004 | Sehl |
| 6,911,496 B2 | 6/2005 | Rhee |
| 6,916,910 B2 | 7/2005 | Wolfinbarger, Jr. |
| 7,025,916 B2 | 4/2006 | Bachrach |
| 7,064,187 B2 | 6/2006 | Stone |
| 7,157,428 B2 | 1/2007 | Kusanagi |
| 7,244,272 B2 | 7/2007 | Lesh |
| 7,314,636 B2 | 1/2008 | Caseres |
| 7,412,978 B1 | 8/2008 | Keller |
| 7,413,752 B2 | 8/2008 | Sawhney |
| 7,575,743 B2 | 8/2009 | Hunziker |
| 7,595,377 B2 | 9/2009 | Stone |
| 7,807,150 B2 | 10/2010 | Griffith |
| 7,883,693 B2 | 2/2011 | Sehl |
| 7,887,599 B2 | 2/2011 | Casares |
| 7,932,354 B2 | 4/2011 | Heimann |
| 8,067,031 B2 | 11/2011 | Daniloff |
| 8,084,055 B2 | 12/2011 | Voytik-Harbin |
| 8,124,120 B2 | 2/2012 | Sadozai |
| 8,455,459 B2 | 6/2013 | Wortzman |
| 8,580,289 B2 | 11/2013 | Seyedin |
| 8,607,044 B2 | 12/2013 | Hallam-Baker |
| 9,149,562 B2 | 10/2015 | Shortkroff |
| 9,480,775 B2 | 11/2016 | Guillen |
| 10,052,407 B2 | 8/2018 | Gleeson |
| 10,111,981 B2 | 10/2018 | DeVore |
| 10,898,497 B2 | 1/2021 | Centeno |
| 11,235,089 B2 | 2/2022 | DeVore |
| 2007/0065943 A1 | 3/2007 | Smith |
| 2008/0188416 A1 | 8/2008 | Bernstein |
| 2009/0012628 A1 | 1/2009 | Shortkroff |
| 2009/0022808 A1 | 1/2009 | Champion |
| 2009/0117188 A1 | 5/2009 | Gershkovich |
| 2010/0172829 A1 | 7/2010 | Anderson |
| 2010/0210588 A1 | 8/2010 | Schwach-Abdellaoui |
| 2010/0217403 A1 | 8/2010 | Champion |
| 2011/0087152 A1 | 4/2011 | David |
| 2011/0301131 A1 | 12/2011 | Fitzpatrick |
| 2015/0147406 A1 | 5/2015 | Robinson |
| 2015/0367029 A1 | 12/2015 | DeVore |
| 2017/0065741 A1 | 3/2017 | Gavard Molliard |
| 2019/0046429 A1 | 2/2019 | Khoshbin |
| 2019/0374457 A1 | 12/2019 | Lee |
| 2020/0197568 A1 | 6/2020 | Lee |
| 2021/0138113 A1 | 5/2021 | Shoseyov |
| 2021/0161672 A1 | 6/2021 | Krom |
| 2022/0362437 A1 | 11/2022 | DeVore |
| 2022/0362438 A1 | 11/2022 | DeVore |
| 2023/0083186 A1 | 3/2023 | DeVore |
| 2023/0201418 A1 | 6/2023 | DeVore |

FOREIGN PATENT DOCUMENTS

| | | |
|---|---|---|
| CN | 109503864 | 3/2019 |
| CN | 109824919 | 5/2019 |
| CN | 110964215 | 4/2020 |
| CN | 111234271 | 6/2020 |
| WO | 1986000079 | 1/1986 |
| WO | 1986000912 | 2/1986 |
| WO | 1990009401 | 8/1990 |
| WO | 2012167226 | 12/2012 |
| WO | 2019241099 | 12/2019 |

OTHER PUBLICATIONS

Nobuhiko, Yui, et al., "Regulated release of drug microspheres from inflammation responsive degradable matrices of crosslinked hyaluronic acid." Journal of Controlled Release, vol. 25, Nos. 1-2, 1993, pp. 133-143.

Reháková, Milena, et al., "Properties of collagen and hyaluronic acid composite materials and their modification by chemical crosslinking." Journal of Biomedical Materials Research, 1996, vol. 30, No. 3, pp. 369-372.

De Vore, Dale P., "Collagen as an Ophthalmic Biomaterial." In Encyclopedic Handbook of Biomaterials & Bioengineering, Part B, Applications, Marcel Dekker, Inc., New York, 1995, Ch. 45, pp. 1233-1260.

Friess, Wolfgang. "Collagen-biomaterial for drug delivery." European Journal of Pharmacokinetics and Biopharmaceuticals, 1998, vol. 45, pp. 113-136.

Kilmer, Claire, et al., "Collagen Type I and II Blend Hydrogel with Autologous Mesenchymal Stem Cells as a Scaffold for Articular Cartilage Defect Repair." ACS Biomater Sci Eng., Jun. 8, 2020, vol. 6, No. 6, pp. 3464-3476.

Nunez, Kristen. "What is Sodium Hyaluronate and How Is It Used in Skin Care?" <https://www.healthline.com/health/beauty-skin-care/sodium-hyaluronate#vs-hyaluronic-acid>, Nov. 6, 2020, 12 pages.

Silver and Garg, Collagen: Characterization, Processing and Medical Applications, In Handbook of Biodegradable Polymers, Eds. Domb, Kost, and Wiseman, Harwood Academic Publishing, Australia, Ch. 17).

Song, Xi. et al, "A Novel Human-Like Collagen Hydrogel Scaffold with Porous Structure and Sponge-like Properties." Polymers, Dec. 31, 2017, No. 12, vol. 19, Article No. 638, pp. 1-17.

Cohen et al. "Artecoll: A Long-Lasting Injectable Wrinkle Filler Material: Report of a Controlled, Randomized, Multicenter Clinical Trial of 251 Subjects." Plastic and Reconstructive Surgery, 114(4), Sep. 15, 2004, pp. 964-976.

Baumann, Leslie, et al. Chapter 23—"Dermal Fillers," in Cosmetic Dermatology—Principles and Practice. McGraw Hill, 2009, pp. 191-211.

(56) References Cited

OTHER PUBLICATIONS

Cockerham, Kimberly, et al., "Collagen-Based Dermal Fillers: Past, Present, Future," Facial Plastic Surgery, vol. 25, No. 2, 2009, pp. 106-113.
Denton, Andrew B. et al., Chapter 13—"Review of Collagen Fillers," in Office-based Cosmetic Procedures and Techniques. Cambridge University Press, 2010, pp. 59-64.
Duan, Wang-ping et. al., "Studies of Articular Cartilage Repair from 2009-2018: A Bibliometric Analysis of Articles." Orthopedic Surgery, vol. 13, 2021, pp. 608-615.
Kontturi, Leena-Stiina, et al., "An Injectable, in situ Forming Type II Collagen/Hyaluronic Acid Hydrogel Vehicle for Chondrocyte Delivery in Cartilage Tissue Engineering." Drug Delivery and Translational Research, 2014, No. 4, pp. 149-158.
Lin, Yung-Kai, et al., "Studies of Novel Hyaluronic Acid-Collagen Sponge Materials Composed of Two Different Species of Type I Collagen," Journal of Biomaterials Applications, 2007, vol. 21, pp. 265-281.
Musumeci, Giuseppe, et. al., "New perspectives for articular cartilage repair treatment through tissue engineering: A contemporary review." World Journal of Orthopedics, Apr. 2014, vol. 5, No. 2, pp. 80-88.
Rehakova, Milena, et al., "Properties of Collagen and Hyaluronic Acid Composite Materials and Their Modification by Chemical Crosslinking," Journal of Biomedical Materials Research, 1996, vol. 30, pp. 369-372.
Rodriguez-Fontain, et al., "In-situ Hydrogel Polymerization for Articular Cartilage Regenration." Rev Asoc Argent Ortop Traumatol, 2019, vol. 84, No. 2, pp. 296-308.
Spiller, Kara L., et al., "Hydrogels for the Repair of Articular Cartilage Defects." Tissue Engineering: Part B, 2011, 1 vol. 7, No. 4, pp. 281-299.
Stuart, Mary. "Cartilage Repair: What's the Right Combination?" Start-Up, vol. 14, No. 8, Sep. 2009, pp. 1-9.
Sulaiman, Shamsul Bin, et al., "Gelatin Microsphere for Cartilage Tissue Engineering: Current and Future Strategies." Polymers, 2020, vol. 12, 16 pages.
Tagle, Jorge M., et. al., "Clinical Performance of a Dermal Filler Containing Natural Glycolic Acid and a Polylactic Acid Polymer," J. Aesthetic and Clinical Dermatology, vol. 3, No. 2, Feb. 5, 2010, pp. 42-47.
Borel and Randoux, "Frontiers in Matrix Biology." vol. 10, In Methods of Connective Tissue Research, Eds. Robert, Moczar, and Moczar, S. Karger, Basel, 1985, pp. 1-58.
Grün, Nicole Gabriele, et al., "Resorbable implants in pediatric fracture treatment." Innovative Surgical Science, 2018; vol. 3, No. 2, pp. 119-125.
Kurowiak, Jagoda, et al., "Biodegradable Polymers in Biomedical Applications: A Review—Developments, Perspectives and Future Challenges." International Journal of Molecular Sciences, 2023, vol. 24, 18 pages.
Landa, Robert, et al., "Principles of Tissue Engineering." 2020, (entire book) 1602 pages.
Lemperle, Gottfried, et al., "ArteFill Permanent Injectable for Soft Tissue Augmentation: I. Mechanism of Action and Injection Techniques." Aesth Plast Surg, 2010, vol. 34, pp. 264-272.
Ratner, Buddy, D. "Degradation of Materials in the Biological Environment." Biomaterials Science, An Introduction to Materials in Medicine, 1997, pp. 695-754.
Simpson, Biomaterials in Reconstructive Surgery, In Collagen as a Biomaterial, C. V. Mosby Co., Ch. 11, 1983, pp. 109-117.
Solomon, Philip, et al., "Facial Soft Tissue Augmentation With Bellafill: A Review of 4 Years of Clinical Experience in 212 Patients." Plastic Surgery, 2021, vol. 29, No. 2, pp. 98-102.
Van Eck, Carola F., et al., "The Classification of Implants: Class I, II, III." Journal of Long-Term Effects of Medical Implants, 2009, vol. 19, No. 3, pp. 185-193.
Shimojo, Andrea A., et al., "The Performance of Crosslinking with Divinyl Sulfone as Controlled by the Interplay Between the Chemical Modification and Conformation of Hyaluronic Acid." J. Braz. Chem. Soc., 2015, vol. 26, No. 3, pp. 506-512.
Guo, Jiahong, et al., "An in situ mechanical adjustable double crosslinking hyaluronic acid/poly-lysine hydrogel matrix: Fabrication, characterization and cell morphology." International Journal of Biological Macromolecules, 2021, vol. 180, pp. 234-241.

\* cited by examiner

HYALURONIC ACID-COLLAGEN COPOLYMER COMPOSITIONS AND MEDICAL APPLICATIONS THEREOF

CROSS REFERENCE TO RELATED APPLICATION

This application claims the benefit of U.S. Provisional Application No. 63/294,164, filed Dec. 28, 2021, which is incorporated herein by reference in its entirety.

FIELD OF THE INVENTION

The present invention relates to glycosaminoglycan-collagen copolymers, such as hyaluronic acid-collagen copolymers and heparosan-collagen copolymer, for medical applications (such as cosmetic medical) including soft tissue augmentation. The copolymer composition may be injected into tissues to correct defects or deficiencies, such as skin wrinkles, scars, and folds in dermal tissues.

BACKGROUND

Injectable materials for augmenting soft tissues have been used for more than 100 years. Mineral oil, paraffin, and similar oils and waxes were used for a variety of purposes in the first two decades of the last century. The first approved compositions for soft tissue augmentation were composed of bovine collagen, and later human collagens. However, collagen-based products are no longer available, due to limits in longevity. The only current FDA approved product containing collagen is Bellafill. The current markets for dermal fillers or products for soft tissue augmentation are dominated by products composed of hyaluronic acid. However, there is still a need, and market demand, for a safe and effective collagen-based product for soft tissue augmentation. The present invention describes the preparation and application of a glycosaminoglycan-collagen copolymer, such as hyaluronic acid or heparosan-collagen copolymer.

Hyaluronic acid was discovered by Meyer and Palmer in 1934. Karl Meyer isolated the polysaccharide from the vitreous humor. Since it contained uronic acid, Meyer named the substance hyaluronic acid from hyaloid (meaning glassy, vitreous) and uronic acid. At physiological pH all carboxyl groups on the uronic acid residue are dissociated and the polysaccharide was named sodium hyaluronate when sodium is the counter ion. In 1986, Balazs suggested the name hyaluronan. This is currently the accepted terminology. The abbreviation "HA" will be used in this application to designate hyaluronan, which includes hyaluronic acid and its metallic salts.

HA is a linear polysaccharide (long-chain biological polymer) formed by repeating disaccharide units consisting of D-glucuronic acid and N-acetyl-D-glucosamine linked by $\beta(1-3)$ and $\beta(1-4)$ glycosidic linkages. HA is distinguished from the other glycosaminoglycans, as it is free from covalent links to protein and sulphuric groups. It is however an integral component of complex proteoglycans. HA is an important component of the intercellular matrix, the material filling the space between the cells of such diverse tissues as skin, tendons, muscles and cartilage.

HA and heparosan are two glycosaminoglycans having similar structures. In particular, heparosan is composed of the same two monosaccharide component sugars as hyaluronan but with different glycosidic bonds (the $\beta1,3$-bond between glucuronic acid and N-acetyl-glucosamine in hyaluronan is replaced by an $\alpha1,4$-bond in heparosan). HA and heparosan exhibit unique viscous flow, elastic and pseudoplastic properties. Other glycosaminoglycans, GAGs, may form viscous solutions, but only at considerably greater concentrations than HA and heparosan. HA has been demonstrated to be important in different activities such as tissue hydration, lubrication, solute transportation, cell migration, cell function, cell differentiation, and cell proliferation.

There are several methods to crosslink hyaluronic acid and other polysaccharides as discussed below. In addition, there have been literature publications and patents describing chemical crosslinking of collagen and hyaluronic acid including Rehakova et. al. (1996) using starch dialdehyde and Lin et al. (2007) using 1-ethyl-3-(3-dimethylaminopropyl-carbodiimide (EDC) and U.S. Pat. No. 8,607,044 (Schroeder, et al., 2014) using divinyl sulfone or 1,4-butanediol diglycidyl ether (BDDE).

Methods for Crosslinking Hyaluronic Acid or Heparosan

U.S. Pat. No. 4,963,666 issued to Malson discloses a process for producing polysaccharides containing carboxyl groups, which comprises, first, reacting a polysaccharide containing carboxyl groups (such as hyaluronic acid) with a bi- or polyfunctional epoxide under a base condition, resulting in a water-soluble, non-gelatinous epoxy-activated polysaccharide, second, removing any un-reacted epoxide by, for example, dialysis, and, third, placing the activated polysaccharide in a mold and allowing it to dry. The epoxy-activated polysaccharides become crosslinked during drying.

U.S. Pat. No. 4,716,224 issued to Sakurai et al. discloses a process for producing crosslinked hyaluronic acid or salt thereof, wherein the crosslinking agent is a polyfunctional epoxy compound including halomethyloxirane compounds and a bisepoxy compound. The crosslinked product has a crosslinking index of 5 to 20 per 100 repeating disaccharide units and is water soluble and stringy.

U.S. Pat. No. 5,017,229 issued to Burns et al. discloses a method for making a water insoluble derivative of hyaluronic acid, comprising combining an aqueous solution of HA with a solid content of 0.4% to 2.6% w/w, a polyanionic polysaccharide, and an activating agent, for example, EDC (1-ethyl-3-(3-dimethylaminopropyl carbodiimide hydrochloride) at pH 4.75 to form a water insoluble hydrogel of hyaluronic acid.

U.S. Pat. No. 5,527,893 issued to Burns et al. discloses a method of making water insoluble derivatives of polyanionic polysaccharides, characterized by an acyl urea derivative of hyaluronic acid added during the crosslinking of HA with EDC, to produce a modified hyaluronic acid hydrogel.

U.S. Pat. No. 5,356,883 issued to Kuo et al. discloses a method for preparing water-insoluble hydrogels, films, and sponges from hyaluronic acid by reacting HA, or a salt thereof, in HA solution with EDC crosslinking agent. After reaction, the product precipitates upon the addition of ethanol, giving a water-insoluble gel.

U.S. Pat. No. 5,502,081 issued to Kuo et al. describes a substance having pharmaceutical activity covalently bonding to the polymer chain of hyaluronic acid through the reaction of a carbodiimide compound.

U.S. Pat. No. 6,013,679 issued to Kuo et al. discloses a method for preparing water insoluble derivatives of hyaluronic acid, wherein carbodiimide compounds are used as crosslinking agents for hyaluronic acid to form water insoluble derivatives.

WO 86/00912 (De Bedler et al.) describes a method for producing a gel for preventing tissue adhesion following surgery, including crosslinking a carboxyl-containing polysaccharide (such as hyaluronic acid) with a bi- or polyfunctional epoxide compound to form a gel of crosslinked hyaluronic acid.

WO 86/00079 (Malson et al.) describes a method of preparing gels of crosslinked HA, in which the crosslinking agent is a bifunctional or polyfunctional epoxide, or a corresponding halohydrin or epihalohydrin or halide. The product obtained is a sterile and pyrogen-free gel of hyaluronic acid.

WO 90/09401 and U.S. Pat. No. 5,783,691 issued to Malson et al. disclose a process for preparing gels of crosslinked hyaluronic acid, characterized by phosphorus-containing reagent use as the crosslinking agent.

U.S. Pat. No. 4,716,154 issued to Malson et al. describes a method for producing gels of crosslinked hyaluronic acid for use as a vitreous humor substitute. The method is characterized by the gels of crosslinked hyaluronic acid being produced with polyfunctional epoxide, or halohydrin or epihalohydrin or halide as a crosslinking agent. The examples show that gels of HA can be formed by adding epoxide, such as BDDE, to basic HA solution when the solid content of HA in HA solution is more than 13.3% and the reaction temperature is higher than 50° C.

Nobuhiko et al., Journal of Controlled Release, 25, 1993, page 133-143, disclose a method for preparing lipid microsphere-containing crosslinked hyaluronic acid. A basic solution of hyaluronic acid in NaOH solution with 20 wt % solid content of hyaluronic acid has suitable amounts of polyglycerol polyglycidyl ether (PGPGE) added to it, PGPGE/repeating units of HA (mole/mole) is about 1.0, and the mixture is reacted at 60° C. for 15 minutes, giving a gel of crosslinked HA.

Nobuhiko et al., Journal of Controlled Release, 22, 1992, page 105-106, disclose a method for preparing gels of crosslinked hyaluronic acid. A basic solution of hyaluronic acid in NaOH solution with 20 wt % solid content of hyaluronic acid has a solution of EGDGE (ethylene glycol diglycidyl ether) or PGPGE epoxide in ethanol added to it, and the mixture is reacted at 60° C. for 15 minutes, giving a gel of crosslinked HA.

U.S. Pat. Nos. 4,582,865 and 4,605,691 issued to Balazs et al. disclose a method for preparing crosslinked gels of hyaluronic acid and products containing such gels. The crosslinked gels of HA are formed by reaction of HA solution and divinyl sulfone as crosslinking agent under the condition of pH above 9.0.

U.S. Pat. No. 4,937,270 issued to Hamilton et al. discloses a method for producing water insoluble HA hydrogels, in which EDC and L-leucine methyl ester hydrochloride are used as crosslinking agents for hyaluronic acid.

U.S. Pat. No. 5,760,200 issued to Miller et al. discloses a method for producing water insoluble derivatives of polysaccharides. An acidic polysaccharide (such as hyaluronic acid) aqueous solution has EDC and L-leucine methyl ester hydrochloride as crosslinking agents for hyaluronic acid added, giving a water insoluble HA gel.

Due to the similar structures and properties of heparosan to HA, the above methods for crosslinking HA can also be used in crosslinking heparosan.

Methods for Crosslinking Hyaluronic Acid or Heparosan to Collagen

There are several methods to crosslink hyaluronic acid and other polysaccharides as discussed below. In particular U.S. Pat. No. 6,150,461 (Takei, et. al.) describes the preparation of a copolymer in which hyaluronic acid is grafted on a polymer main chain. The main chain is this case is a poly-L-lysine (PLL). The hyaluronic acid graft has a molecular weight of less than 100,000, preferably between 1,000 and 50,000. The purpose of the hyaluronic acid-PLL is to deliver DNA or drugs to appropriate tissues or cells containing hyaluronic acid binding sites. Hyaluronic acid is polymerized to PLL by reductive amination in a high salt buffer.

In addition there have been literature publications and patents describing chemical crosslinking of amino group or carboxy group of collagen and the carboxy group of hyaluronic acid including Rehakova et al. (1996) using starch dialdehyde and Lin et al. (2007) using 1-ethyl-3-(3-dimethylaminopropyl-carbodiimide (EDC) and U.S. Pat. No. 8,607,044 (Schroeder, et al., 2014) using divinyl sulfone or 1,4-butanediol diglycidyl ether (BDDE).

Due to the similar structures and properties of heparosan to HA, the above methods for crosslinking HA to Collagen can also be used in crosslinking heparosan to Collagen.

SUMMARY OF THE INVENTION

The present invention describes a novel method to crosslink glycosaminoglycans, such as hyaluronic acid or heparosan, to collagen resulting in a soluble, injectable preparation of the glycosaminoglycan-collagen copolymer. These crosslinked glycosaminoglycan-collagen copolymer (such as hyaluronic acid-collagen) compositions are intended for use in soft tissue augmentation including treating dermal defects and deficiencies The inventors have discovered that PLL can be used to derivatize hyaluronic acid or heparosan molecules with pendent amine groups. The resultant PLL substituted hyaluronic acid/heparosan can be used to crosslink similar molecules using difunctional acetylation chemicals. More importantly, the PLL derivatized hyaluronic acid or heparosan molecules can be polymerized with collagen via covalent crosslinking between free amines on hyaluronic acid or heparosan and collagen. Acylation reactions will proceed as long as the pendant free amines are in deprotonated form (accomplished by adjusting the solution pH to the pKa of the pendant ε-amine groups (about 8.5). The resultant polymerized hyaluronic acid-collagen or heparosan-collagen will remain in soluble form and will exhibit enhanced stability when exposed to hyaluronidase. The soluble form of HA-Collagen or heparosan-Collagen copolymer ensures injectability of the copolymer in the application in soft tissue augmentation. And the enhanced stability of the copolymer is expected to improve the longevity of the copolymer in vivo for soft tissue augmentation.

Amido bonds are the most prevalent chemical bonds found in natural organic molecules and various biomolecule such as peptide, proteins, DNA and RNA. The resonating structures are highly stable and adopt particular three-dimensional structures. HA-collagen or heparosan-collagen copolymer in present invention is highly biocompatible in rabbit intracutaneous irritation test.

In some aspect of the present application, provided herein is a method for preparing a glycosaminoglycan-soluble collagen copolymer comprising the steps of: a) chemically grafting poly-L-lysine to the glycosaminoglycan by reacting the glycosaminoglycan with PLL; b) chemically derivatizing soluble collagen by reacting collagen solution at alkaline pH with an acetylation agent; c) mixing the glycosaminoglycan-PLL gel with derivatized collagen gel; d) adding bifunctional acetylation agents to react with free amine groups on glycosaminoglycan-PLL and derivatized collagen to produce a mixture of glycosaminoglycan-PLL-Collagen, polymerized glycosaminoglycan-PLL and polymerized derivatized collagen gel, wherein the glycosaminoglycan is selected from hyaluronic acid, heparosan or any combinations thereof.

In some embodiments, the hyaluronic acid is produced by microbial fermentation using *Streptococcus* species or *Bacillus* species, or allogeneic or animal tissues (including rooster combs, human umbilical cord, bovine synovial fluid or vitreous humor) derived hyaluronic acid.

In some embodiments, the hyaluronic acid or heparosan is a salt such as a sodium salt or a potassium salt with a molecular weight ranging from 150,000 to 2 million Daltons, preferably 1-1.4 million Daltons.

In some embodiments, the soluble collagen is derivatized with a compound selected from the group consisting of sulfonic acids, sulfonyl chlorides, and acid chlorides including glutaric anhydride. In some embodiments, the soluble collagen is extracted, isolated, and purified from bovine, porcine, human collagen, recombinant human collagen, recombinant collagen peptides or collagen mimic peptides from microbial fermentation.

In some embodiments, in step (a), the PLL is dissolved in sodium borate buffer; and/or the PLL is in a concentration of 0.1M; and/or step (a) is carried out at a pH ranging from 8.0-9.0, preferably 8.5. In some embodiments, in step (b) the collagen pKa is reduced and ε-amino groups of lysine residues is deprotonated. In some embodiments, in step (c), the pH is adjusted to about 9.0-9.5, preferably 9.5. In some embodiments, the method further comprises e) adjusting the pH of the polymerized gel to neutral pH (such as 6.8-7.4); and/or wherein step (a) is carried out before, after or simultaneously to step (b)

In some embodiments, the concentration of hyaluronic acid or heparosan is 1-3% (w/v); and/or the concentration of collagen is 1-5% (w/v); and/or the ratio of hyaluronic acid or heparosan to collagen ranges from 1:10~10:1 (w/w), preferably 1:5~5:1 (w/w).

In some aspects of the present application, provided herein is a glycosaminoglycan-PLL-Collagen copolymer, wherein the glycosaminoglycan is selected from hyaluronic acid, heparosan or any combinations thereof.

In some embodiments, the copolymer is prepared according to the method of the present application. In some embodiments, the ratio of glycosaminoglycan to collagen ranges from 1:10~10:1 (w/w), preferably 1:5~5:1 (w/w).

In some aspects of the present application, provided herein is a method for augmenting soft tissue in a subject in need thereof comprising injecting the copolymer of the present application to the site in need of the augment.

In some embodiments, the composition is injected into soft tissue to correct soft tissue deficiencies. In some embodiments, the composition is injected into dermis to correct soft tissue deficiencies including wrinkles, dermal folds, dermal laxity, unevenness, facial emaciation, fat atrophy, cheek depression, eye socket depression, or a combination thereof. In some embodiments, the composition is injected into tissues other than dermis, including cartilage, to correct tissue deficiencies. In some embodiments, the composition is injectable through a 25~30 gauge needle or cannula, such as a 25, 27 or 30 gauge needle or cannula.

BRIEF DESCRIPTION OF THE DRAWINGS/FIGURES

In the following, aspects of the invention will be elucidated by means of examples, with reference to the drawings. The drawings are diagrammatic and may not be drawn to scale. The following drawings form part of the present specification and are included to further demonstrate certain aspects of the present invention. The invention may be better understood by reference to one or more of these drawings in combination with the detailed description of specific embodiments presented herein.

FIG. 1 shows Fluorescein stained Diglutaryl Chloride Crosslinked Hyaluronic Acid Gels. FIG. 1A: a droplet of free acid fluorescein dissolved in 0.1M sodium phosphate buffer (pH 7.2) was added to 2 mL of HA-PLL-collagen polymerized using 10% ethylenediaminetetraacetic dianhydride. FIG. 1B: fluorescein stained HA-PLL-collagen/ethylenediaminetetraacetic dianhydride gel upon injected through a 27G needle into 2 mL of 0.1M sodium phosphate buffer. FIG. 1C: fluorescein stained HA-PLL-collagen/ethylenediaminetetraacetic dianhydride gel in 2 mL of 0.1M sodium phosphate buffer for more than 30 days. Arrows show the fluorescein stained diglutaryl chloride crosslinked hyaluronic acid gels.

Figure 2:
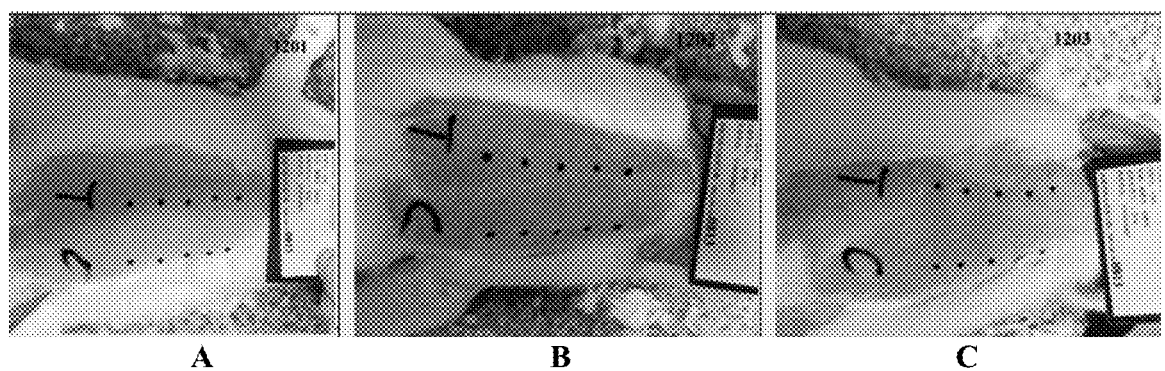

FIG. 2 shows rabbit intracutaneous irritation evaluation results of HA-PLL-collagen (T for test article and C for control, photo taken at 72 hours after injection). FIGS. 2A, 2B and 2C show the results of three rabbits, respectively.

DETAILED DESCRIPTION

The first step in the process is to polymerize poly-L-lysine (PLL) to hyaluronic acid. The resultant copolymer can then be reacted with appropriate bifunctional acylation agents to crosslink free amine groups on the pendant PLL. Acylation reactions will proceed as long as the pendant free amines are in depronatated form (accomplished by adjusting the solution pH to the pKa of the pendant ε-amine groups (about 8.5). It is believed that the resultant polymerized hyaluronic acid will remain in soluble form (as opposed to the particulate form of Restylane and CTA) and will exhibit enhanced stability when exposed to hyaluronidase.

Hyaluronic can be prepared by fermentation. Molecular weights may range from as low as 25,000 Daltons to more than 3 million Daltons.

Collagen can be derived from bovine, porcine, fish, human, or recombinant human sources. Recombinant collagen peptides or collagen mimic peptides from microbial fermentation can also be used. Soluble collagen is chemically derivatized using an acylating agent using methods described by DeVore, et. al. (U.S. Pat. Nos. 4,713,446, 4,851,513, 4,969,912, 5,067,961, 5,104,957, 5,201,764, 5,219,895, 5,332,809, 5,354,336, 5,476,515, 5,480,427, 5,631,243, and 6,161,544). Method will be described in the Examples.

PLL hydrobromide may have a molecular weight from 500 Daltons (such as Sigma Catalog Number P 8954) to more than 300,000 Daltons (such as Sigma Catalog Number P 5899).

Bifunctional or multifunctional acylating agents may include the following coupling agents which have two or three groups which react with amines but do not react with carboxyl groups. Such coupling agents include di- and tri-carboxylic acid halides, di- and tri-sulfonyl halides, di- and tri-anhydrides, di- and tri-reactive active esters and coupling agents containing at least two groups of the carboxylic acid halide, sulfonyl halide, anhydride or active ester type. Preferred aromatic and aliphatic di- and tri-carboxylic acid halides include d-camphoric diacid chloride; 4-p-(o-chlorocarbonylbenzoyl)phenyl]butyryl chloride; furan-3,5-dicarboxylic chloride; fumaryl chloride; glutaryl chloride; succinyl chloride; sebacoyl chloride; isophthaloyl chloride; terephthaloyl chloride; 4-bromoisophthaloyl chloride; diglycolic diacid chloride; 1,1-cyclohexanediacetyl chloride; 2,2-dimethyl glutaryl chloride; thioglycolic acid dichloride; nitrilo triacetyl chloride; beta-methyl carballylic acid trichloride; hexadecanedioic acid dichloride; malonic acid dichloride; acetone dicarboxylic acid dichloride; oxydiacetyl chloride benzene-1,3,5-tricarbonyl chloride; 4-chlorocarbonylphenoxyacetyl chloride; homo phthaloyl chloride; 4,4'-diphenyl ether dicarboxylic acid dichloride; 4,4'-diphenylthioetherdicarboxylic acid dichloride; 4,4'-diphenylsulfonedicarboxylic acid dichloride; acetylene dicarboxylic acid dichloride; cyclohexane-1,4-dicarboxylic acid dichloride; trans-3,6-endomethylene-1,2,3,6-tetrahydrophthaloyl chloride; 4,4'-dithiodibutyryl chloride; diphenylmethane-4,4'-bis(oxyacetyl) chloride; N-(4-chlorocarbonylphenyl) anthranyloyl chloride; 1,3-benzenebisoxyacetyl chloride; pyridine-3,5-dicarboxylic acid dichloride; pyridine-2,5-dicarboxylic acid dichloride; pyridine-2,4-dicarboxylic acid dichloride; pyrazine-2,3-dicarboxylic acid dichloride; and pyridine-2,6-dicarboxylic acid dichloride; ethyleneglycol bis-4-chlorocarbonylphenyl) ether; diethyleneglycol bis-4-chlorocarbonylphenyl) ether; bis-4-chlorocarbonyl-2-tolyl)thioether; and N-chlorocarbonylmethyl-N-methylglutaramic acid chloride.

Preferred aromatic and aliphatic di- or trisulfonyl halides include para-fluorosulfonylbenzenesulfonyl chloride; 1,3,5-benzenetrisulfonyl chloride; 2,6-naphthalenedisulfonyl chloride; 4,4'-biphenyl disulfonyl chloride; 1,10-decanedisulfonyl chloride; and 4,4'-trans-stilbenedisulfonyl chloride.

Preferred di- and trianhydride coupling agents include 1,2,4,5-benzenetetracarboxylic dianhydride; 3,4,9,10-perylene tetracarboxylic dianhydride; 3,3',4,4'-benzophenonetetracarboxylic dianhydride; 1,2,7,8-naphthalenetetracarboxylic dianhydride; pyromellitic dianhydride; 2,3,4,5-tetrahydrofurantetracarboxylic acid dianhydride; mellitic trianhydride; 1,2,3,4-cyclobutanetetracarboxylic dianhydride; bicyclo[2,2,2]oct-7-ene-2,3,5,6-tetracarboxylic dianhydride; cyclopentanetetracarboxylic dianhydride; ethylenediaminetetraacetic dianhydride; and diethylenetriaminepentaacetic dianhydride.

Preferred coupling agents containing combinations of amine-reactive groups include 5-chlorosulfonyl-ortho-anisic acid chloride; 2-chloro-5-fluorosulfonylbenzoyl chloride; 4-chlorosulfonylphenoxyacetyl chloride; meta-fluorosulfonylbenzoyl chloride; and trimellitic anhydride acid chloride.

The concentration of the coupling agent is dependent upon many factors including the reactivity of the coupling agent. In general, however, the amount of the coupling agent is about 1 to 30% (w/v or v/v) of coupling agent per unit volume of HA-PLL-derivatized collagen, preferably about 5% to 25% (w/v or v/v) of coupling agent per unit volume of HA-PLL and more preferably about 10% to 20% (w/v or v/v) of coupling agent per unit volume of HA-PLL-derivatized collagen. Preferably, in order to limit the degree of coupling, the reaction mixture contains purified collagen in a concentration of 0.05 to 0.3 percent by weight, and more preferably 0.15 to 0.3 percent by weight.

The pH of the reaction mixture is preferably maintained throughout the coupling reaction at about 8 to 11, preferably at about 9.0 to 10.0, and most preferably at about 9.5, by addition of a dilute base, e.g., in sodium hydroxide. In this manner, almost all of the lysine epsilon amino groups present on the HA-PLL molecules and derivatized collagen molecules are freed from their protonated form, and become capable of reaction with either the coupling agent.

The above descriptions are mainly based on HA. Due to the similar structures and properties between HA and heparosan, HA in the present disclosure can be replaced by heparosan to obtain a copolymer with similar properties and functions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Preparation of PLL Grafted to HA

One gram of LifeCore hyaluronic acid (1.01~1.8 million Daltons) and 100 milligrams of PLL were dissolved in 150 ml of sodium borate buffer (0.1M, pH 8.5) containing 1M NaCl. Sodium borohydride solution (NaBH$_3$CN; in borate buffer) was added directly to the mixture to a concentration of 25 mM. The mixture was stirred and incubated at room temperature for 48 hours. The reactant was then dialyzed against 0.5M NaCl for 3 days. The molecular weight of the hyaluronic acid component was approximately $1.5 \times 10^6$ Daltons. PLL was purchased from Sigma Aldrich (poly-L-lysine hydrobromide, molecular weight 4,000-15,000 Daltons.

Example 2. Preparation of Derivatized Collagen

Two hundred milliliters of 3 mg/mL purified, soluble collagen (Porcogen, Lot #531131080) was filtered through 0.45 μm and 0.2 μm cartridge filters. The filtered collagen was placed in a 500 ml beaker and the pH was adjusted to 9.0 using 10N and 1N NaOH. After stirring for 5 minutes at room temperature, pulverized glutaric anhydride powder (Sigma, >95%) was slowly added to the stirring collagen solution at a concentration equal to 10% of the collagen (60 mg). The pH of the collagen solution was maintained at pH 9.0 by addition of drops of 10N NaOH. The glutaric anhydride reaction continued for 15 minutes at which point drops of 6N HCl and 1N HCl were added to reduce the pH to approximately 4.5 to precipitate the derivatized collagen. The derivatized collagen was then placed in 50 mL centrifuge tubes and centrifuged at 3500-5000 rpm to precipitate the derivatized collagen. The recovered precipitate was then solubilized by adjusting the pH to 7.2 by adding drops of 10N NaOH and 1N NaOH. The pH was monitored as the NaOH was mixed with the derivatized collagen pellet. The neutralized, clear and transparent collagen gel was then placed in 50 mL centrifuge tubes and centrifuged to remove air bubbles.

Example 3. Polymerization of HA-PLL and Derivatized Collagen Using Bifunctional Acylation Agents-Diglutaryl Chloride or EDTA Dianhydride HA-PLL solutions were prepared at about 1% (w/v) (HA). Derivatized collagen was prepared at 3% (w/v) collagen. The HA-PLL and derivatized collagen were adjusted to pH 9.5 and the mixture stirred for 15 minutes. A transparent, viscous solution was formed. The mixture was crosslinked with 1% diglutaryl chloride solution. The solution was dialyzed against 0.04M sodium phosphate buffer containing 0.9% NaCl. The solution was then isolated from the dialysis tubing and stored at 2 to 8° C. The second crosslinked HA-PLL and derivatized collagen solution were crosslinked by reacting the HA-PLL solution with 10% ethylenediaminetetraacetic dianhydride (Sigma Aldrich Chemical Company, 97%). Resultant HA-PLL and derivatized collagen solutions were transparent and very thick (gel-like). The product was dialyzed against 0.04M sodium phosphate buffer containing 0.9% NaCl. The product was then isolated from the dialysis tubing and stored at 2 to 8° C.

Example 4. Visual Examination of Diglutaryl Chloride Polymerized HA-PLL Derivatized Collagen Compositions (HA-PLL-Collagen)

A droplet of free acid Fluorescein dissolved in 0.1M sodium phosphate buffer (pH 7.2) was added to 2 mL of HA-PLL-collagen polymerized using diglutaryl chloride. Fifty microliters (50 μL) of the fluorescein stained HA-PLL-collagen/diglutaryl chloride gel was injected through a 27G needle into 2 mL of 0.1M sodium phosphate buffer to evaluate the appearance of the compositions. The droplet formed a continuous thread upon injection and maintained physical structure for more than 30 day.

Example 5. Visual Examination of Ethylenediaminetetraacetic Dianhydride Polymerized HA-PLL Derivatized Collagen Compositions (HA-PLL-Collagen)

A droplet of free acid fluorescein dissolved in 0.1M sodium phosphate buffer (pH 7.2) was added to 2 mL of HA-PLL-collagen polymerized using 10% ethylenediaminetetraacetic dianhydride (FIG. 1A). Fifty microliters (50 μL) of the fluorescein stained HA-PLL-collagen/ethylenediaminetetraacetic dianhydride gel was injected through a 27G needle into 2 mL of 0.1M sodium phosphate buffer to evaluate the appearance of the compositions (FIG. 1). The droplet formed a continuous thread upon injection (FIG. 1B) and maintained physical structure for more than 30 days (FIG. 1C). This copolymer showed excellent cohesive properties which now is considered to contribute to augmentation result.

Example 6. Rabbit Intracutaneous Irritation Test on Ethylenediaminetetraacetic Dianhydride Polymerized HA-PLL Derivatized Collagen Composition (HA-PLL-Collagen)

Rabbit intracutaneous irritation test is a biocompatibility test required by ISO 10993 standards. The HA-PLL-collagen was evaluated for the potential to cause irritation following intracutaneous injection into New Zealand White Rabbits. The quintuple extraction of HA-PLL-collagen was prepared in sterile 0.9% NaCl solution under 37° C. for 72 hours. Sterile 0.9% NaCl solution was used as a negative control. Hairs on both sides of the spine of three health New Zealand white rabbits were removed to have a sufficient area for five injection sites on each side at least 4 hours before injection. 0.2 mL of HA-PLL-collagen extraction and negative control were injected in each site and erythema/oedema was observed at 24 hours, 48 hours and 72 hours after injection according to the ISO standard. And the irritations of HA-PLL-Collagen and negative control were zero (Table 1). No irritation evidence was detected (FIG. 2: FIG. 2A: #1201, FIG. 2B, #1202, and FIG. 2C, #1203).

TABLE 1

Results of Rabbit intracutaneous irritation test

| Extract Solution | Animal # | Dose | Reaction | 24 h | 36 h | 72 h |
|---|---|---|---|---|---|---|
| In Sterile 0.9% NaCl (SC) | 1201 | Test article | erythema | 0 | 0 | 0 |
| | | | oedema | 0 | 0 | 0 |
| | | Negative control | erythema | 0 | 0 | 0 |
| | | | oedema | 0 | 0 | 0 |
| | 1202 | Test article | erythema | 0 | 0 | 0 |
| | | | oedema | 0 | 0 | 0 |
| | | Negative control | erythema | 0 | 0 | 0 |
| | | | oedema | 0 | 0 | 0 |
| | 1203 | Test article | erythema | 0 | 0 | 0 |
| | | | oedema | 0 | 0 | 0 |
| | | Negative control | erythema | 0 | 0 | 0 |
| | | | oedema | 0 | 0 | 0 |

Final Intracutaneous Irritation Score: 0

All references, including patents, publications, and patent applications, mentioned in this specification are herein incorporated by reference in the same extent as if each independent publication, patent or patent application was specifically and individually indicated to be incorporated by reference.

Thus, while there has been disclosed what is presently believed to be the preferred embodiments of the invention, those skilled in the art will appreciate that other and further changes and modifications can be made without departing from the scope or spirit of the invention, and it is intended that all such other changes and modifications are included in and are within the scope of the invention as described in the appended claims.

REFERENCES

Publications

Yui Nobuhiko; Nihira Jun; Okano Teruo; Sakurai Yasuhisa (1993). Regulated release of drug microspheres from inflammation responsive degradable matrices of crosslinked hyaluronic acid., 25 (1-2), 133-143. doi: 10.1016/0168-3659 (93) 90102-b Yui Nobuhiko; Okano Teruo; Sakurai Yasuhisa (1992). *Inflammation responsive degradation of crosslinked hyaluronic acid gels.,* 22 (2), 105-116. doi: 10.1016/0168-3659 (92) 90195-w Meyer, K. and Palmer, J. W. (1934) The polysaccharide of the vitreous humor. Journal of Biological Chemistry, 107, 629-634.

Reháková M, Bakos D, Vizárová K, Soldán M, Juricková M. Properties of collagen and hyaluronic acid composite materials and their modification by chemical crosslinking. J Biomed Mater 1996 Res. Mar; 30 (3): 369-72. doi: 10.1002/(SICI) 1097-4636 (199603) 30:3<369:: AID-JBM11>3.0.CO;2-F. PMID: 8698700.

Lin Y K, Liu D C. Studies of novel hyaluronic acid-collagen sponge materials composed of two different species of type I collagen. J Biomater Appl. 2007 January; 21 (3): 265-81. doi: 10.1177/0885328206063502. Epub 2006 Mar. 16. PMID: 16543285.

Patents

U.S. Pat. No. 4,141,973
U.S. Pat. No. 4,784,990
U.S. Pat. No. 5,099,013
U.S. Pat. No. 5,166,331

U.S. Pat. No. 5,316,926
U.S. Pat. No. 5,411,874
U.S. Pat. No. 5,559,104
U.S. Pat. No. 5,925,626
U.S. Pat. No. 4,963,666
U.S. Pat. No. 4,716,224
U.S. Pat. No. 5,017,229
U.S. Pat. No. 5,527,893
U.S. Pat. No. 5,356,883
U.S. Pat. No. 5,502,081
U.S. Pat. No. 6,013,679
WO 86/00912 (De Bedler et al.)
WO 86/00079 (Malson et al.)
WO 90/09401 and U.S. Pat. No. 5,783,691
U.S. Pat. No. 4,716,154
U.S. Pat. Nos. 4,582,865 and 4,605,691 issued to Balazs et al
U.S. Pat. No. 4,937,270 issued to Hamilton et al
U.S. Pat. No. 5,760,200 issued to Miller et al.
U.S. Pat. No. 6,150,461 (Takei, et. al.)
U.S. Pat. No. 8,607,044
U.S. Pat. No. 4,713,446
U.S. Pat. No. 4,851,513
U.S. Pat. No. 4,969,912
U.S. Pat. No. 5,067,961
U.S. Pat. No. 5,104,957
U.S. Pat. No. 5,201,764
U.S. Pat. No. 5,219,895
U.S. Pat. No. 5,332,809
U.S. Pat. No. 5,476,515
U.S. Pat. No. 5,480,427
U.S. Pat. No. 5,631,243
U.S. Pat. No. 6,161,544

The invention claimed is:

1. A method for preparing a glycosaminoglycan-soluble collagen copolymer comprising the steps of:
   a) chemically grafting poly-L-lysine (PLL) to the glycosaminoglycan by reacting the glycosaminoglycan with PLL to produce a glycosaminoglycan-PLL gel;
   b) chemically derivatizing soluble collagen by reacting a collagen solution at an alkaline pH with an acetylation agent to produce a collagen gel derivative;
   c) mixing the glycosaminoglycan-PLL gel with the collagen gel derivative; and
   d) adding a bifunctional acetylation agent to react with free amine groups on glycosaminoglycan-PLL and collagen gel derivative to produce a mixture of glycosaminoglycan-PLL-collagen gel, glycosaminoglycan-PLL polymer, and collagen gel derivative polymer,
   wherein the glycosaminoglycan is selected from hyaluronic acid, heparosan, a salt of hyaluronic acid, a salt of heparosan, and combinations thereof.

2. The method of claim 1, wherein the hyaluronic acid is from microbial fermentation using *Streptococcus* species or *Bacillus* species, or allogeneic tissue, or animal tissue.

3. The method of claim 1, wherein the salt of hyaluronic acid or heparosan has a molecular weight from 150,000 to 2 million Daltons.

4. The method of claim 3, wherein the hyaluronic acid or heparosan is a sodium salt or a potassium salt; or the molecular weight of the hyaluronic acid or heparosan is 1-1.4 million Daltons.

5. The method of claim 1, wherein the acetylation agent for chemically derivatizing the soluble collagen is selected from the group consisting of sulfonic acid, sulfonyl chloride, acid chloride, and glutaric anhydride.

6. The method of claim 1, wherein the soluble collagen is from (i) bovine, (ii) porcine, (iii) human collagen, (iv) recombinant human collagen, (v) recombinant collagen peptides, or (vi) collagen mimic peptides from microbial fermentation, via extracting, isolating, and purifying.

7. The method of claim 1, wherein in step (a), the PLL is dissolved in sodium borate buffer; the PLL is in a concentration of 0.1M; or step (a) is at a pH range of 8.0-9.0.

8. The method of claim 7, wherein the pH is 8.5.

9. The method of claim 1, wherein in step (b) comprises reducing collagen pKa and deprotonating ε-amino groups of lysine residues.

10. The method of claim 1, wherein step (c) comprises adjusting the pH to about 9.0-9.5.

11. The method of claim 1, wherein the method further comprises e) adjusting the pH of the collagen gel derivative polymer to neutral pH; or wherein step (a) is before, after or simultaneously to step (b).

12. The method of claim 11, wherein the pH is 6.8 to 7.4.

13. The method of claim 1, wherein the concentration of hyaluronic acid or heparosan is 1-3% (w/v); the concentration of collagen is 1-5% (w/v); or the ratio of hyaluronic acid or heparosan to collagen is from 1:10 to 10:1 (w/w).

14. The method of claim 13, wherein the ratio is 1:5 to 5:1 (w/w).

15. A method for preparing a hyaluronic acid-soluble collagen copolymer comprising the steps of:
   a) chemically grafting poly-L-lysine (PLL) to hyaluronic acid by reacting the hyaluronic acid with PLL to produce a hyaluronic acid-PLL gel;
   b) chemically derivatizing soluble collagen by reacting a collagen solution at an alkaline pH with an acetylation agent to produce a collagen gel derivative;
   c) mixing the hyaluronic acid-PLL gel with the collagen gel derivative; and
   d) adding a bifunctional acetylation agent to react with free amine groups on hyaluronic acid-PLL and collagen gel derivative to produce a mixture of hyaluronic acid-PLL-collagen gel, hyaluronic acid-PLL polymer, and collagen gel derivative polymer.

16. The method of claim 15, further comprising preparing the hyaluronic acid from fermentation.

17. The method of claim 15, wherein the hyaluronic acid has a molecular weight from 150,000 to 2 million Daltons.

18. The method of claim 15, wherein step (b) comprises derivatizing the soluble collagen with an acetylation agent selected from the group consisting of sulfonic acid, sulfonyl chloride, and acid chloride.

19. The method of claim 15, further comprising extracting, isolating, and purifying the soluble collagen from bovine, porcine, or human collagen.

20. A method for preparing a hyaluronic acid-soluble collagen copolymer comprising the steps of:
   a) chemically grafting poly-L-lysine (PLL) to hyaluronic acid by reacting the hyaluronic acid with PLL to produce a hyaluronic acid-PLL gel;
   b) chemically derivatizing soluble collagen by reacting a collagen solution at an alkaline pH with an acetylation agent to produce a collagen gel derivative;
   c) mixing the hyaluronic acid-PLL gel with the collagen gel derivative; and
   d) adding a bifunctional acetylation agent to react with free amine groups on hyaluronic acid-PLL and collagen gel derivative to produce a mixture of hyaluronic acid-PLL-collagen gel, hyaluronic acid-PLL polymer, and collagen gel derivative polymer, wherein the hyaluronic acid is a metallic salt of hyaluronic acid.

21. The method of claim 20, wherein the hyaluronic acid has a molecular weight from 150,000 to 2 million Daltons.

* * * * *